US009182363B2

(12) United States Patent
Chen

(10) Patent No.: US 9,182,363 B2
(45) Date of Patent: Nov. 10, 2015

(54) INSTRUMENT AND METHOD OF MEASURING THE CONCENTRATION OF A TARGET ELEMENT IN A MULTI-LAYER THIN COATING

(71) Applicant: Xunming Chen, Bedford, MA (US)

(72) Inventor: Xunming Chen, Bedford, MA (US)

(73) Assignee: OLYMPUS NDT, INC., Waltham, MA (US)

( * ) Notice: Subject to any disclaimer, the term of this patent is extended or adjusted under 35 U.S.C. 154(b) by 69 days.

(21) Appl. No.: 14/079,968

(22) Filed: Nov. 14, 2013

(65) Prior Publication Data

US 2014/0140473 A1 May 22, 2014

Related U.S. Application Data

(60) Provisional application No. 61/727,350, filed on Nov. 16, 2012.

(51) Int. Cl.
*G01N 23/223* (2006.01)
(52) U.S. Cl.
CPC ........ *G01N 23/223* (2013.01); *G01N 2223/076* (2013.01); *G01N 2223/61* (2013.01); *G01N 2223/633* (2013.01)

(58) Field of Classification Search
USPC .............................................. 378/45, 44, 50
See application file for complete search history.

(56) References Cited

U.S. PATENT DOCUMENTS

| | | | | |
|---|---|---|---|---|
| 5,274,688 A | * | 12/1993 | Grodzins | 378/45 |
| 5,396,529 A | | 3/1995 | Grodzins | |
| 2009/0067572 A1 | * | 3/2009 | Grodzins et al. | 378/45 |

\* cited by examiner

*Primary Examiner* — Phillip A Johnston
*Assistant Examiner* — Hsien Tsai
(74) *Attorney, Agent, or Firm* — Ostrolenk Faber LLP

(57) ABSTRACT

An instrument and a method of detecting a target element in a multi-layer thin coating. Lα, Lβ and Lγ x-rays are caused to be emitted from the target element (preferably lead paint) with excitation radiation. Upon detecting the emitted x-rays, an areal concentration of the target element is calculated using Lα and Lβ intensities once, and then using the Lβ and Lγ intensities once, by reference to a single layer model; By combining the two concentrations calculated using single layer model, a more accurate concentration can be calculated for the target element in the multi-layered surface coating.

18 Claims, 4 Drawing Sheets

INSTRUMENT AND METHOD OF MEASURING THE CONCENTRATION OF A TARGET ELEMENT IN A MULTI-LAYER THIN COATING

CROSS-REFERENCE TO RELATED APPLICATION

This application claims the benefit and priority of U.S. Provisional patent application Ser. No. 61/727,350 filed Nov. 16, 2012 entitled AN INSTRUMENT WITH IMPROVEMENT IN DETECTION OF MULTI-LAYER THIN COATING, the entire disclosure of which is incorporated herein by reference.

BACKGROUND OF THE DISCLOSURE

The instant invention is directed to an instrument and method of measuring the concentration of a target element in a multi-layer, thin coating and, more particularly, to such an instrument and method that is capable of measuring non-destructively the lead concentration on a surface coating.

Lead paint was used widely around 1920 due to its durability. Later, lead pigments were found to be a health hazard. It was banned from use since 1978. Old buildings need to be checked for lead paint to make sure it is safe for kids, thus it is necessary to have a non-destructive method for detecting the lead concentration from a surface.

A lead K line based instrument can be used to measure the lead concentration. K lines have very high energy (75 keV and 85 keV). They can travel through many layers of covering material with very little loss. Thus, by simply measuring the K line x-ray intensity, lead concentration can be determined. However, many drawbacks are associated with K line based instruments. Thus:

(a) First, K line x-ray intensity is very weak and the measurement error can be large (when the test time is fixed). When the lead concentration is low (around 1 mg/cm$^2$), the large statistical error makes the reading unreliable.

(b) Even if the lead paint is on the opposite side of the wall or is covered by another layer of dry wall (after deleading), lead can still be detected, erroneously reporting a lead hazard when it is totally safe.

(c) A radioactive isotope source is present (needed to generate high energy x-rays to excit lead K shell electrons).

(d) L line x-rays have much less energy. Its escape depth is much shorter. Ten layers of regular paints on top of lead paint will reduce the lead L line intensities by more than 90%. Thus an L line based instrument is a surface lead detector. For single-layered lead paint, there is a well established method for measuring the surface lead concentration from lead Lα and Lβ lines (as described in U.S. Pat. No. 5,274,688 and U.S. Pat. No. 5,396,529). The lead paint can be on top of the surface or buried by non-lead containing material, and this method works accurately. However, when the paint contains multiple layers of lead paint, the method fails badly.

(e) The current action level for deleading is 1.0 mg/cm$^2$ and the trend is moving lower. Thus the most critical lead range is from 0 to 1.5 mg/cm$^2$. In this range, the large statistic error of K line based reading is a real problem. On the other hand, buildings that are 100 years old are likely to have multiple layers of lead paint, the limitation of the lead L line based prior art makes the instrument based on the technology useless for those buildings.

The present disclosure provides a solution that targets the needs of and meets the following primary objectives:

(a) Reliably and non-destructively determining whether or not the amount of lead is less than the action level (current action level is 1.0 mg/cm$^2$);

(b) Handling both single layer and multi-layer lead paint coatings; and (c) Operate without using a radioactive source.

SUMMARY BACKGROUND OF THE DISCLOSURE

The foregoing and other objects of the invention are realized via a method of measuring an areal concentration of a target element coated by more than one layer near the surface of a substrate, where the target element is capable of emitting Lα, Lβ and Lγ when suitably excited. In accordance with a preferred embodiment, the method comprises the step of:

a) inducing the Lα and Lβ and Lγ x-rays to be emitted from said target element with excitation radiation;

b) detecting said Lα, Lβ and Lγ x-rays and determine the intensity of the Lα, Lβ and Lγ x-rays separately;

c) calculating the areal concentration of said target element by means of the following equation:

$$m_1 = I_{L\beta}/A1/I_{L\beta S} \qquad \text{Eq. 1}$$

wherein $m_1$ is the calculated target element concentration based on single layer model using Lα and Lβ intensities; A1 is the absorption factor computed from the Lα, Lβ intensity ratio (during calibration, A1 as a function of Lα, Lβ intensity ratio is fitted as a curve; and this curve is used later to calculate the A1 from measured Lα,Lβ intensity ratio), $I_{L\beta}$ is the measured Lβ line intensity of the target element from sample under testing; $I_{L\beta S}$ is the Lβ intensity of the target element from a NIST standard without any shielding layers.

$$m_2 = I_{L\gamma}/A2/I_{L\gamma S} \qquad \text{Eq. 2}$$

wherein $m_2$ is the calculated target element concentration based on single layer model using Lβ and Lγ. A2 is the absorption factor computed from the Lβ, Lγ intensity ratio (during calibration, A2 as a function of Lβ, Lγ intensity ratio is fitted as a curve; and this curve is used later to calculate the A1 from measured Lα, Lβ intensity ratio), $I_{L\gamma}$ is the measured Lγ line intensity from sample under testing; $I_{L\gamma S}$ is the Lγ intensity of the target element from a NIST standard without any shielding layers; and d) calculating the combine areal concentration of said target element according to:

$$m_z = m_2 + C_3(m_2 - m_1) \qquad \text{Eq. 5}$$

wherein $C_3$ is a constant determined during an instrument calibration, and $m_z$ is the lead concentration emitted from the at least one layer of coating containing the target element.

Preferably, the method of the invention includes using a filter to reduce low energy x-rays associated with excitation radiation and, further preferably, the filter is selected from a plurality of filters provided on a filter wheel. Also, if in the method of the invention it is initially determined that $m_1$ is substantially equal to $m_2$, then the areal concentration is reported based on $m_1$. The invention also concerns the instrument that implements the aforedescribed method of detecting a target element in a multi-layer thin coating.

DESCRIPTION OF THE PREFERRED EMBODIMENTS

Figure 1:
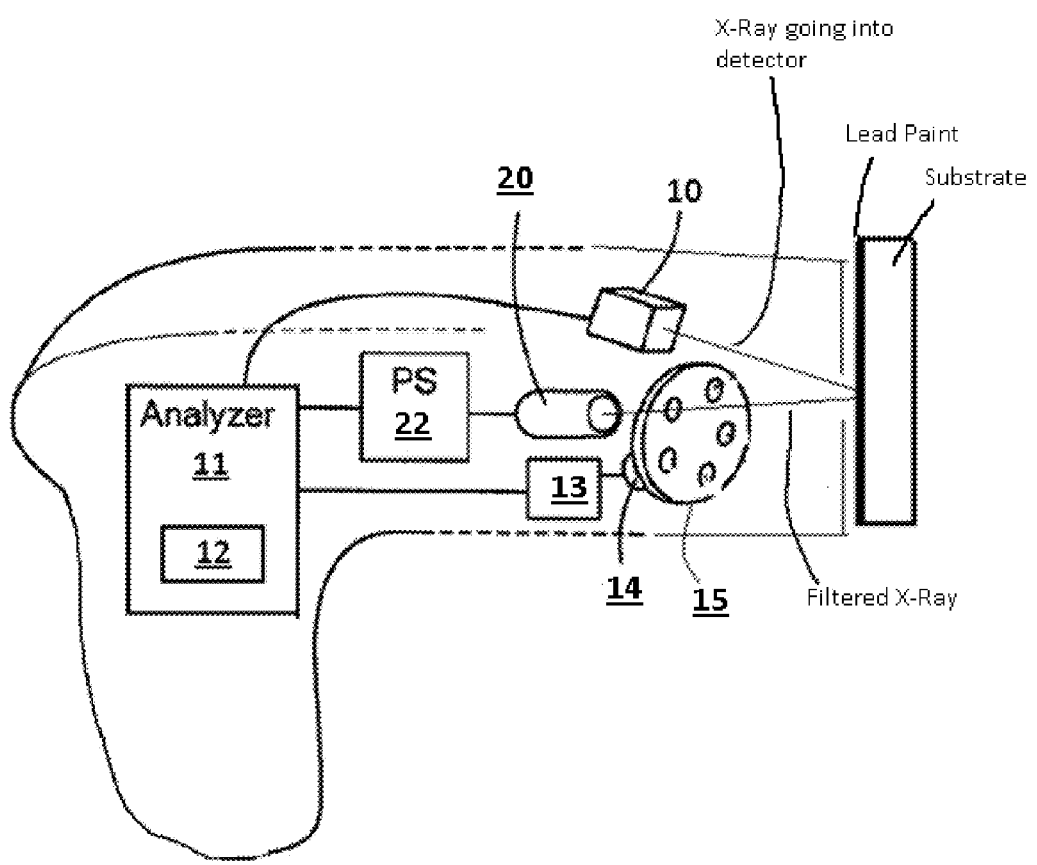
FIG. 1 illustrates an embodiment of the invention, both diagrammatically and pictorially.

FIG. 1 is a schematic diagram of an XRF instrument according to the present invention. As can be seen, the XRF instrument includes a power supply 22; an x-ray tube 20; an x-ray detector 10; a filter assembly 14; a filter wheel 15 with a few different x-ray filters; and an analyzer 11 which includes an improved lead paint module 12 according to the presently disclosed invention. In addition, the instrument preferably includes a component 13 which is controlled by analyzer 11 to select a filter from the filter wheel 15. During an operation, x-rays are generated by x-ray tube 20, to energize a substrate with one or more layers of coating containing material which is the subject of detection. The x-rays are sensed by detector 10, which generates data which it provides to analyzer 11.

During a test, the instrument is placed against a substrate having the lead paint. The analyzer 11 sets the voltage and current of the power supply 22. The x-ray tube 20 then generates x-rays when the power supply is turned on. In the meantime, the analyzer 11 controls component 13 to select the proper filter from filter wheel 15. The generated x-rays are filtered by the x-ray filter 15. The filtered x-rays reach the lead paint on the substrate.

Figure 2:
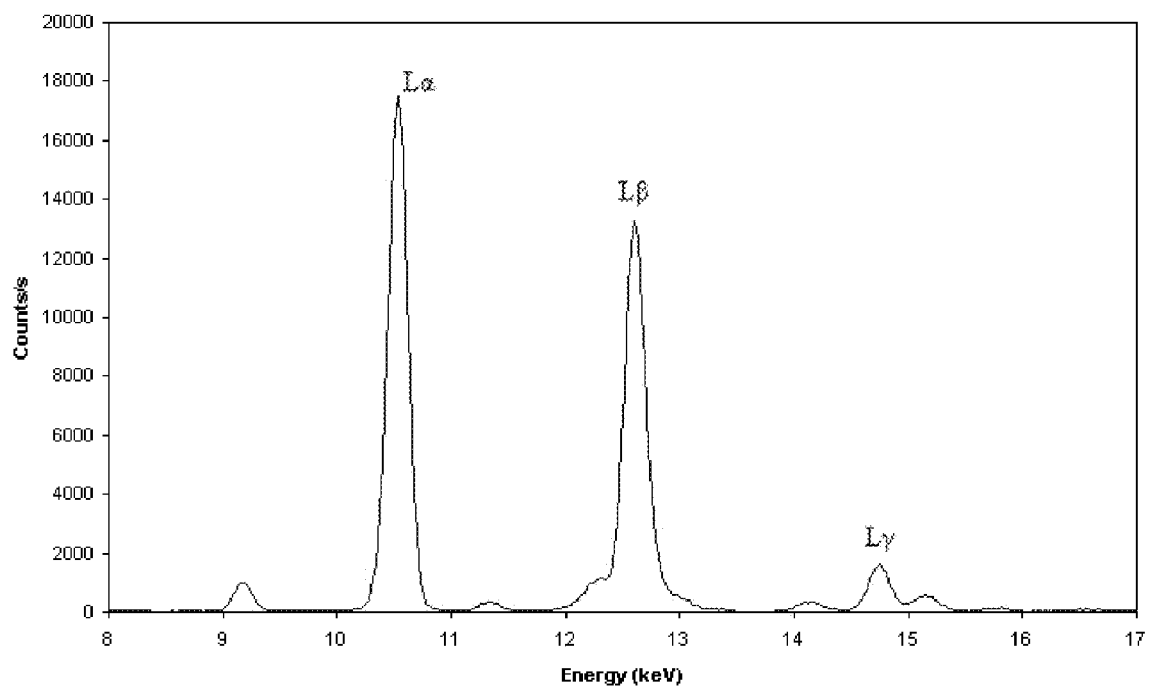
FIG. 2 is a chart showing aspects of the invention.

Lead L lines (L$\alpha$, L$\beta$, L$\gamma$) will be then induced by the incident x-rays. The lead L lines pass though overlying material and some of them will reach the detector 10 and be detected. The x-rays going into the detector 10 contain lead L lines. FIG. 2 shows a typical x-ray spectrum from lead paint. It has lead lines L$\alpha$, L$\beta$ and L$\gamma$.

Referring to FIG. 2, the X-axis represents the energy of the x-rays in keV, while the Y-axis represents the intensity of x-rays in counts per second. The graph shows the energy distribution of x-rays detected by detector 10. L$\alpha$, L$\beta$ and L$\gamma$ are x-ray fluorescence lines from lead. L$\alpha$ has an energy of 10.5 keV; L$\beta$ has an energy of 12.6 keV and L$\gamma$ has an energy of 14.8 keV. The tube voltage (around 40 kV) and current are supplied by power supply 22. They are optimized to maximize the generation of lead L lines. x-ray filter 15 is used to cut down the low energy x-rays from the tube 20 because they do not help creating lead L line, and instead introduce noise in the lead L line regions. Proper selection of the filter significantly improves the signal noise ratio in lead L line regions. In FIG. 2, the lead L line peaks have almost no background due to the proper use of x-ray filter 15.

Because L$\alpha$, L$\beta$ and L$\gamma$ have different energies, they have different mean free path and absorption coefficients. Thus the measured L$\alpha$/L$\beta$ or L$\beta$/L$\gamma$ ratios will be different depending on how deeply the lead is buried. In other words, L$\alpha$/L$\beta$ or L$\beta$/L$\gamma$ is a function of the total absorption of the layer between the lead and the surface. By mapping out the relationship between L$\alpha$/L$\beta$ and the total absorption during calibration, one can find the absorption of the covering layer based on the L$\alpha$/L$\beta$ ratio. Suppose the calculated absorption is A1 based on L$\alpha$/L$\beta$ ratio, then the lead concentration, according to existing practice, is:

$$m_1 = I_{L\beta} A1 / I_{L\beta S} \qquad \text{Eq. 1}$$

wherein $I_{L\beta}$ is the measured L$\beta$ line intensity from the sample under testing; $I_{L\beta S}$ is the lead L$\beta$ intensity from NIST (National Institute of Standards and Technology) standard with 1.0 mg/cm$^2$ lead concentration (recorded during instrument calibration), herein the "L$\beta$ NIST intensity".

Similarly, one can calculate the lead concentration $m_2$ based on L$\beta$ and L$\gamma$.

$$m_2 = I_{L\gamma} A2 / I_{L\gamma S} \qquad \text{Eq. 2}$$

wherein $I_{L\gamma}$ is the measured L$\gamma$ line intensity from the sample under testing; $I_{L\gamma S}$ is the lead L$\gamma$ intensity from NIST standard with 1.0 mg/cm$^2$ lead concentration), herein the "L$\gamma$ NIST intensity".

If the lead paint is single layered, $m_1$ and $m_2$ should be equal to each other regardless of whether the lead paint is buried or not. However, according to the observation of the present inventor, when there is more than one layer of lead paint, this model breaks down. $m_1$ and $m_2$ then significantly underreport the lead concentration.

Noticing that $m_1$ or $m_2$ fails to provide accurate lead concentration when more than one layer of lead is encountered, the following steps are employed to provide a method that guides accurate lead concentration values or measurements.

To calculate the lead concentration for multi-layered lead paint, one treats the plain paint in the middle of lead paint layers as a perturbation to the single layered model. The plain paint within a multi-layer lead paint sandwich changes the amount of lead detected. To a first order approximation, this change is proportional to the amount of plain paint inserted $$\Delta m_1 = m_z - m_1 = C_1 f(\text{paint}) \qquad \text{Eq. 3}$$

$$\Delta m_2 = m_z - m_2 = C_2 f(\text{paint}) \qquad \text{Eq. 4}$$

wherein $\Delta m_1$ is the difference between the expected lead concentration $m_z$ and the calculated lead concentration $m_1$ based on single layer model using L$\alpha$ and L$\beta$ lines; $\Delta m_2$ is the concentration difference based on L$\beta$ and L$\gamma$ calculation; C1 and C2 are unknown constants;

f(paint) is an unknown function related to lead distribution within the multi-layer lead paint.

From equation 2 and 3, one obtains: $f(\text{paint}) = m_1 - m_2/C_1 - C_2$. Thus $$m_z = m_2 + C_2 f(\text{paint}) = m_2 + C_3(m_2 - m_1) \qquad \text{Eq. 5}$$

Where $$C_3 = \frac{C_2}{C_1 - C_2}$$

is a constant that can be determined by the following steps: 1) Making a multi-layer lead paint with known concentration $m_z$; 2) Acquiring an x-ray spectrum from this multi-layer lead paint; and 3) calculating $m_1$ and $m_2$ using Eq. 1 and Eq. 2; and 4) calculating $C_3$ from Eq. 5.

Once $C_3$ is determined, it can be used on all instruments because it is independent of any given instrument. Then we can calculate the lead concentration based on the above equations, with $m_z$ being the lead concentration calculated from the multi-layer model, $m_1$ is the calculated lead concentration based on single layer model using $L\alpha$ and $L\beta$ intensities; and $m_2$ is the calculated lead concentration based on single layer model using $L\beta$ and $L\gamma$.

Figure 3:
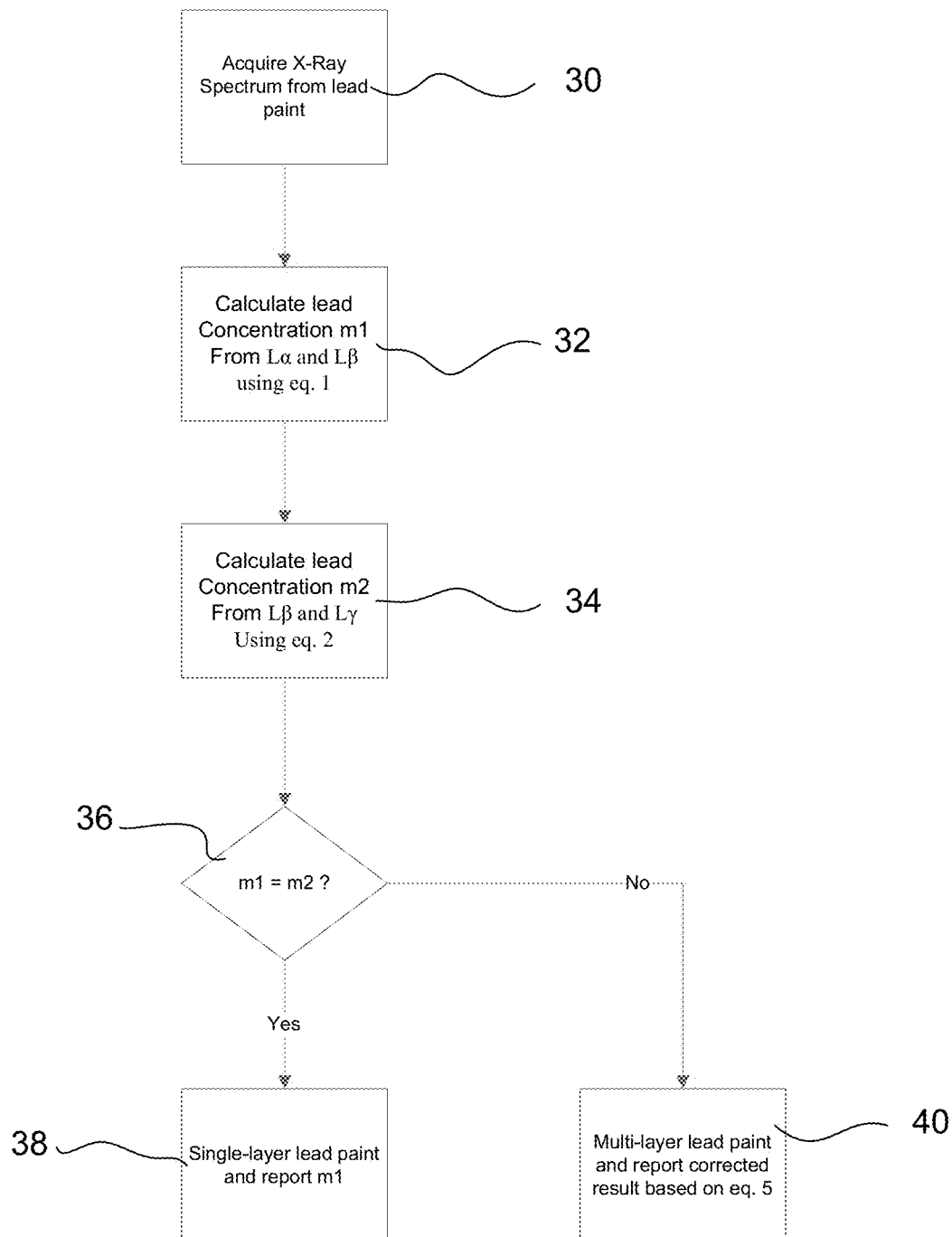
FIG. 3 is a block diagram of the invention.

Reference is now made to FIG. 3, which shows a flow chart of the steps employed by the present disclosure leading to a more accurate lead detection, particularly when multiple layers of lead paint are involved. During a test, any x-ray spectrum from lead paint is acquired in step 30; Lead concentration m1 is calculated based on $L\alpha$ and $L\beta$ using Eq. 1 as shown in step 32; Lead concentration $m_2$ is calculated based on $L\beta$ and $L\gamma$ using Eq. 2 in step 34; If $m_1$ and $m_2$ are equal to each other, step 36 concludes that the lead paint is single-layered and proceeds to step 38 to report lead concentration m1 based on Eq. 1; If $m_1$ and $m_2$ are different from each other of step 36, it is concluded that the lead paint is multi-layered and the method takes step 40 to report lead concentration based on Eq. 5.

Figure 4:
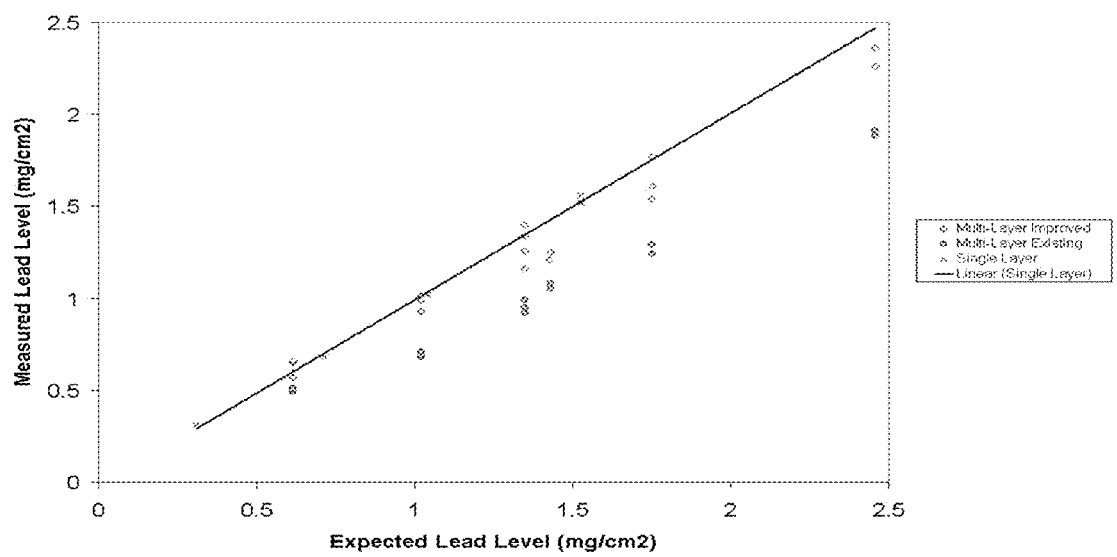
FIG. 4 is a plot of measured lead levels against expected lead levels under different conditions.

FIG. 4 shows how the correction improves the measured lead result: the instrument was calibrated using single layer lead paint. The line in the picture shows the calibration curve of the instrument. Multi-layer samples were made from single layer lead paint standards with blank layers in between.

To check the performances in the critical concentration range of 0 to 2 mg/cm$^2$, single layer lead paint standards were used as test samples. The following table shows the comparison of L line results using the prior single layer lead paint algorithm, K line results and the improved L line results. "Prior L Line Algorithm Reading" and "K Line Reading" are from an isotope instrument based on prior art (see U.S. Pat. No. 5,274,688).

| Standard (mg/cm$^2$) | Prior L Line Reading (mg/cm$^2$) | Precision (mg/cm$^2$) | K Line reading (mg/cm$^2$) | Precision (mg/cm$^2$) | Improved L Line Reading (mg/cm$^2$) | Precision (mg/cm$^2$) |
|---|---|---|---|---|---|---|
| 0.00 | 0.00 | 0.02 | −0.37 | 0.46 | 0.00 | 0.00 |
| 0.71 | 0.70 | 0.10 | 0.23 | 0.45 | 0.67 | 0.02 |
| 1.04 | 1.10 | 0.10 | 0.60 | 0.40 | 1.04 | 0.02 |
| 1.53 | 1.50 | 0.10 | 1.10 | 0.50 | 1.56 | 0.03 |

One should notice that the error of K line based reading is very large, making it almost useless for lead measurement below 1.5 mg/cm$^2$.

The following data is part of the record taken during lead inspection of an old building:

| Unit | Surfaces Tested | Prior Art L Lines (mg/cm2) | K Lines (mg/cm2) | Improved Algorithm L Lines (mg/cm$^2$) | Comments |
|---|---|---|---|---|---|
| 143 B | Kitchen N wall, plaster | 0.26 | 2.30 | 2.23 | |
| 143 B | Kitchen E wall, plaster | 0.3 | 1.90 | 1.49 | |
| 143 B | Kitchen W wall, plaster | 0.4 | 2.00 | 1.58 | |
| 143 B | Bath ceiling, plaster | 0.13 | 1.40 | 0.35 | Large K error |
| | Bath ceiling | 0.13 | 1.3/Prec 0.5 | 0.9 | Large K error |
| | Bath ceiling | 0.16 | 1.1/Prec1.4 | 0.52 | |
| | | | | 0.65 | |
| 327 | Kitchen N wall, plaster ¼" sheetrock laminate | 0.00 | 1.80 | 0.00 | Covered by ¼ sheetrock |
| 327 | LR window casing, wood, E wall - 1/" luan laminate | 0.40 | 7.10 | 2.89 | Covered by ¼ wood |
| 327 | BR 1 window casing, wood N wall - ¼" wood laminate | 0.50 | 8.30 | 8.97 | Covered by ¼ wood |
| 347 | Kitchen N wall, plaster | 0.08 | 8.90 | 3.61 | |
| 347 | Kitchen E wall, plaster | 0.60 | 8.10 | 4.60 | |
| 347 | Kitchen W wall, plaster | 0.80 | 8.70 | 2.79 | |
| 347 | Kitchen door casing to Den | 0.50 | 13.00 | 4.28 | |
| 347 | LR baseboard, wood, W wall | 0.50 | 12.80 | 2.69 | |
| 347 | LR window sill, wood | 1.40 | 8.20 | 10.83 | |
| 347 | LR window sash, metal | 0.00 | −0.50 | 0.00 | |
| 347 | LR closet door, wood, int | 0.90 | 11.80 | 3.90 | |
| 347 | LR patio door casing - chip top | 0.04 | 17.40 | 2.36 | |
| | LR patio door casing - chip bottom | 10.10 | 19.10 | 15.00 | |
| 347 | Bath S upper & lower wall, plaster | 0.40 | 9.90 | 2.21 | |

The paint from this building has multiple layers of lead paint and they are deeply buried. L line reading based on prior art could hardly detect any lead. K line reading detected lead, but its error is 0.5 mg/cm² or higher. If the lead concentration is from 0.5 to 1.5 mg/cm², it will have a hard time classifying whether or not lead is present. With the improved algorithm and optimized instrument settings, we can detect lead from 0 to 2 mg/cm² accurately, the invention method and instrument provide reliable lead positive/negative indications in the high concentration region.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of measuring an areal concentration of a target element coated by more than one layers near the surface of a substrate, the target element capable of emitting Lα, Lβ and Lγ x-rays when suitably excited, the method comprising the steps of:
    a) inducing the $L_\alpha$ and $L_\beta$ and $L_\gamma$ x-rays to be emitted from said target element with excitation radiation;
    b) detecting said $L_\alpha$, $L_\beta$ and $L_\gamma$ x-rays and determining the intensity of the $L_\alpha$, $L_\beta$ and $L_\gamma$ x-rays separately;
    c) calculating the areal concentration of said target element by means of the following equations:

$$m_1 = I_{L\beta}/A1/I_{L\beta S} \quad \text{Eq. 1}$$

wherein $m_1$ is the calculated lead concentration based on single layer model using $L_\alpha$ and $L_\beta$ intensities; A1 is the absorption factor computed from the $L_\alpha$, $L_\beta$ intensity ratio, wherein during calibration, A1 as a function of $L_\alpha$, $L_\beta$ intensity ratio is fitted as a curve; and this curve is used later to calculate the A1 from measured $L_\alpha$, $L_\beta$ intensity ratio; $I_{L\beta}$ is the measured $L_\beta$ line intensity of the target element from sample under testing; $I_{L\beta S}$ is the $L_\beta$ intensity of the target element from a NIST standard without any shielding layers;

$$m_2 = I_{L\gamma}/A2/I_{L\gamma S} \quad \text{Eq. 2}$$

wherein $m_2$ is the calculated lead concentration based on single layer model using $L_\beta$ and $L_\gamma$ intensities; A2 is the absorption factor computed from the $L_\beta$, $L_\gamma$ intensity ratio, wherein during calibration, A2 as a function of $L_\beta$, $L_\gamma$ intensity ratio is fitted as a curve; and this curve is used later to calculate the A1 from measured $L_\alpha$, $L_\beta$ intensity ratio; $I_{L\gamma}$ is the measured $L_\gamma$ line intensity of the target element from sample under testing; $I_{L\gamma S}$ is the $L_\gamma$ intensity of the target element from a NIST standard without any shielding layers; and
    d) calculating the combine areal concentration of said target element according to:

$$m_z = m_2 + C_3(m_2 - m_1) \quad \text{Eq. 5}$$

wherein $C_3$ is a constant determined during an instrument calibration, and $m_z$ is the target element concentration emitted from the at least one layer of coating containing the target element.

2. The method of measuring an areal concentration of a target element of claim 1, wherein the target element is comprised of one or more layers of another material that do not contain the target element.

3. The method of measuring an areal concentration of a target element of claim 1, wherein the target element is lead paint.

4. The method of measuring an areal concentration of a target element of claim 1, wherein the Lα, Lβ and Lγ for the target element have x-ray fluorescent lines with an energy of 10.5 keV, 12.6 keV and 14.8 keV, respectively.

5. The method of measuring an areal concentration of a target element of claim 1, further including using a filter to reduce low energy x-rays associated with the excitation radiation.

6. The method of measuring an areal concentration of a target element of claim 5, including using a filter wheel to select an optimal filter to reduce the low energy x-rays.

7. The method of measuring an areal concentration of a target element of claim 1, including using an x-ray tube to generate the excitation radiation.

8. The method of measuring an areal concentration of a target element of claim 1, including comparing $m_1$ to $m_2$ and, if $m_1$ is substantially equal to $m_2$, reporting the areal concentration based on $m_1$.

9. The method of measuring an areal concentration of a target element of claim 1, including carrying out measurements of the areal concentration of the target element in a range from 0 to 2 mg/cm² and beyond.

10. An instrument configured as an x-ray fluorescence analyzer for measuring an areal concentration of a target element coated by more than one layers near a surface of a substrate, the target element capable of emitting Lα, Lβ and Lγ x-rays when suitably excited, the instrument comprising:
    a) a source of excitation radiation capable of inducing the Lα and Lβ and Lγ x-rays to be emitted from said target element;
    b) a detector configured to detect said Lα, Lβ and Lγ x-rays and determine the intensity of the Lα, Lβ and Lγ x-rays separately;
    c) a calculating unit configured to calculate the areal concentration of said target element by means of the following equations:

$$m_1 = I_{L\beta}/A1/I_{L\beta S} \quad \text{Eq. 1}$$

wherein $m_1$ is the calculated lead concentration based on single layer model using Lα and Lβ intensities; A1 is the absorption factor computed from the Lα, Lβ intensity ratio, $I_{L\beta}$ is the measured Lβ line intensity of the target element; and $I_{L\beta S}$ is the lead Lβ intensity based on a NIST (National Institute of Standards and Technology) standard with 1.0 mg/cm² lead concentration, recorded during instrument calibration, $$m_2 = I_{L\gamma}/A2/I_{L\gamma S} \quad \text{Eq. 2}$$

wherein $m_2$ is the calculated lead concentration based on single layer model using Lβ and Lγ; A2 is the absorption factor computed from the Lβ, Lγ intensity ratio, $I_{L\gamma}$ is the measured Lγ line intensity from sample under testing; and $I_{L\gamma S}$ is the lead Lγ intensity from NIST standard with 1.0 mg/cm² lead concentration; and
    d) further calculating the combined areal concentration of said target element according to:

$$m_z = m_2 + C_3(m_2 - m_1) \quad \text{Eq. 5}$$

where $C_3$ is a constant determined during an instrument calibration, $m_z$ is the target element concentration emitted from the at least one layer of coating containing the target element.

11. The instrument of claim 10, wherein the target element is comprised of one or more layers of another material that do not contain the target element.

12. The instrument of claim 10, wherein the target element is lead paint.

13. The instrument of claim 10, wherein the Lα, Lβ and Lγ for the target element have x-ray fluorescent lines with an energy of 12.6 keV and 14.8 keV, respectively.

14. The instrument of claim 10, further including using a filter to reduce low energy x-rays associated with the excitation radiation.

15. The instrument of claim 10, further including a filter wheel to select an optimal filter to reduce the low energy x-rays.

16. The instrument of claim 10, including an x-ray tube to generate the excitation radiation.

17. The instrument of claim 10, wherein the calculating unit is configured to compare $m_1$ to $m_2$ and, if $m_1$ is substantially equal to $m_2$, reporting the areal concentration based on $m_1$.

18. The instrument of claim 10, wherein said instrument is configured to carry out measurements of the areal concentration of the target element in a range from 0 to 2 mg/cm$^2$ and beyond.

\* \* \* \* \*